United States Patent
Gomez Rivas et al.

(10) Patent No.: US 8,480,958 B2
(45) Date of Patent: Jul. 9, 2013

(54) NANOANTENNA AND USES THEREOF FOR BIOSENSING

(75) Inventors: Jaime Gomez Rivas, Eindhoven (NL);
Ruth W. I. De Boer, Den Bosch (NL);
Olaf Janssen, Geldrop (NL); Arun Narayanaswamy, Chennai (IN); Erik M. H. P. Van Dijk, Hertogenbosch (NL); Marcus Verschuuren, Tilburg (NL)

(73) Assignee: Stichting IMEC Nederland, Eindhoven (NL)

( * ) Notice: Subject to any disclaimer, the term of this patent is extended or adjusted under 35 U.S.C. 154(b) by 0 days.

(21) Appl. No.: 13/466,961

(22) Filed: May 8, 2012

(65) Prior Publication Data
US 2012/0220471 A1 Aug. 30, 2012

Related U.S. Application Data

(60) Division of application No. 12/965,543, filed on Dec. 10, 2010, now abandoned, which is a continuation of application No. PCT/IB2009/052411, filed on Jun. 8, 2009.

(30) Foreign Application Priority Data

Jun. 11, 2008 (EP) .................................... 08305244

(51) Int. Cl.
*G01N 21/64* (2006.01)

(52) U.S. Cl.
USPC ....... 422/82.08; 422/82.07; 73/579; 977/762; 436/172

(58) Field of Classification Search
None
See application file for complete search history.

(56) References Cited

U.S. PATENT DOCUMENTS

2005/0142605 A1 6/2005 Malak
2008/0066549 A1 3/2008 Oldham et al.

OTHER PUBLICATIONS

International Search Report dated Aug. 21, 2009 for PCT/IB2009/052411.
Agren et al, Modeling of multi-photon-induced photoluminescence from organic fluorophores and metal-coated semiconductor nanoparticles, Biophotonics, Nanophotonics and Metamaterials, IEEE International Symposium on Metamaterials, Jan. 1, 2007.
Klunder et al, A novel nano-photonics biosensor concept for rapid molecular diagnostics, Progress in biomedical optics and imaging, SPIE, vol. 6691, pp. 69910P-1, Jan. 1, 2008.
Lippitz et al, Third-harmonic generation from single gold nanoparticles, Nano Letters, ACS, vol. 5, No. 4, pp. 799-802, Apr. 1, 2005.
Muskens et al, Enhanced light extraction from emitters close to clusters of resonant plasmonic nanoantennas, Materials Science and Engineering B, Elsevier, vol. 149, No. 3, pp. 216-219, Apr. 15, 2008.

(Continued)

*Primary Examiner* — Robert Xu
(74) *Attorney, Agent, or Firm* — Knobbe Martens Olson & Bear LLP (57) ABSTRACT

A metal nanoantenna for use in a biosensing device is disclosed. The metal nanoantenna is arranged to exhibit at least two particle plasmon resonances or surface plasmon resonances (SPRs). The nanoantenna is for use in a sensor and allows detection at low concentration of biological components. In one aspect, the nanoantenna can have an asymmetric structural configuration and spectrally separated resonances. In one aspect, there is a location in its structure providing local electromagnetic field enhancement at all of the SPRs. The metal nanoantenna can be used for background free measuring of a quantity of a biological component.

12 Claims, 3 Drawing Sheets

OTHER PUBLICATIONS

Muskens et al, Strong enhancement of the radiative decay rate of emitters by single plasmonic nanoantennas, Nano Letters, ACS, vol. 7, No. 9, pp. 2871-2875, Sep. 1, 2007.

Wei et al, Designing plasmonic nanomaterials as sensors of biochemical transport, E-Journal of Surface Science and Nanotechnology, Surface Science Technology of Japan, vol. 4, pp. 9-18, Jan. 12, 2006.

Giannini, V. et al. "Excitation and emission enhancement of single molecule fluorescence through multiple surface-plasmon resonances on metal trimer nanoantennas", 2008, Optical Society of America, vol. 33(9), pp. 899-901.

NANOANTENNA AND USES THEREOF FOR BIOSENSING

CROSS REFERENCE TO RELATED APPLICATIONS

This application is a divisional of co-pending U.S. patent application Ser. No. 12/965,543 filed Dec. 10, 2010, which is a continuation of PCT Application No. PCT/IB2009/052411, filed Jun. 8, 2009. Each of the above applications is incorporated by reference hereby in its entirety.

BACKGROUND OF THE INVENTION

1. Field of the Invention

The present invention relates to antenna structures, sensors using such structures, to a sensor array using such sensors, e.g. for detecting the presence of a target analyte, and in particular to sensors and sensor arrays where a target analyte is detected based on a detection of the photoluminescence of labels coupled to surface plasmon resonances (SPR). Moreover, the invention relates to an optical detection system comprising such antennas, sensors or sensor arrays, and to a method for detecting the presence of a target analyte using the sensor or sensor array.

2. Description of the Related Technology

Detecting low concentrations of a biological component (a "target") in a fluid such as a liquid analyte mixture is a challenge. Often this is accomplished by selectively capturing the target with a binding composition, which is attached to a solid surface. Whether or not binding has occurred is detected by measuring the presence of a label that has either previously been attached to the target, or is linked to a second binding composition that binds to the captured target. Often the label is fluorescent such that detection is achieved by optical means in the linear regime. Two main elements determine the minimum target concentration that can still be detected. The first important factor is the detection sensitivity of the label. The more sensitive the detection the lower the number of bound labels that is needed before a positive identification can take place. The second factor is the presence of background signals, in particular signals from unbound labels. In the current state of the art these problems are often solved by first letting the binding reaction take place, and then washing away all the unbound labels before starting the detection of the bound labels. This is however undesirable since it increases the complexity of the assay and the measurement time. Different methods have been proposed to allow specific detection of the bound analyte for instance via the use of confocal excitation to reduce the excitation volume to an area of ~1 μm above the surface. When very high background signals are expected this method is not sufficient.

Multi-photon absorption is a non-linear optical absorption process in which two or more photons, either of the same frequency or of different frequencies, are absorbed by a material to reach an excited state. The radiative relaxation from this excited state produces a photon with a higher frequency (shorter wavelength) than the exciting photons. Since the excitation occurs via a virtual state, linear absorption (one photon absorption) and emission of photons with emission at a lower frequency is forbidden. Two-photon absorption is a third-order nonlinear optical process, described by the third order non-linear optical susceptibility. The very low values of optical susceptibility of most materials means that two-photon absorption was of little interest. With the availability of suitable light sources (e.g. short-pulse lasers) and materials with large two-photon absorption cross sections (e.g. semiconductor quantum dots), this process is now receiving attention for technological applications in different fields such as solar energy generation and biophotonics. In a two-photon luminescence (TPL) measurement, the luminescence intensity scales quadratically with the excitation intensity. Significant two photon signals are obtained when the intensity is high, which has lead to the development of the powerful imaging technique of two photon luminescence microscopy for biological applications.

The intensity of luminescence $I_{2\text{-}pho}$ in a two photon excitation process is given by $$I_{2\text{-}pho} = \text{const} \cdot Pex^2 \Delta t$$

where Pex is the power of the pump and $\Delta t$ is the time of the exposure to the pump light.

In the case of a pulsed laser source $I_{2\text{-}pho}$ is given by $$I_{2\text{-}pho} = \text{const} \cdot Pex^2 \Delta t / (\tau \cdot f),$$

where $\tau$ is the pulse duration and f is the laser repetition rate. For a mode-locked Ti:Sapphire laser providing a pulse train with a repetition rate of 80 MHz and a pulse duration of 200 fs, the two-photon fluorescence intensity is 62500 times larger than when a continuous wave (cw) laser with the same power is used. This difference can be compensated by increasing the power of the pump cw laser by a factor of 250. In this way, two photon absorption imaging of biomolecules has been demonstrated using cw lasers instead of with ultra short pulse lasers.

To make two-photon imaging and bio-sensing feasible at continuous wave excitation and low laser powers (<10 mwatt) is has been necessary to develop nanostructures which can locally increase the pump intensity due to resonant processes. Fluorescent probes in the proximity of these structures will exhibit modified properties. The optimization of these properties for biotechnology, the so-called radiative decay engineering, is nowadays in the centre of the research interest. Conductive nanostructures such as nanoantennas have been demonstrated to be very efficient local field enhancers due to the resonant excitation of particle plasmons polaritons or collective oscillations of free charge carriers. In the following we will refer to particle plasmon polariton resonanced as surface plasmon resonances (SPRs). Field enhancements of several orders of magnitude close to the metal surface have been predicted and measured in various structures. Enhancement of the two photon fluorescence of dyes in the proximity of silver nanoparticle fractal clusters has been demonstrated. Two photon luminescence using the field enhancement in single metallic nanorods have been used recently for in vivo imaging of vessels. Two photon luminescence detection of labelled proteins near silver colloid surfaces has been also reported.

SUMMARY OF CERTAIN INVENTIVE ASPECTS

Certain inventive aspects relate to antenna structures, sensors using such structures, a sensor array using such sensors, e.g. for detecting the presence of a biocomponent or "target", and in particular sensors and sensor arrays where a target is detected based on the detection of the photoluminescence of labels coupled to a surface plasmon resonance (SPR). Certain inventive aspects further relate to an optical detection system comprising such antennas, sensors or sensor arrays, and a method for detecting the presence of a target using the sensor or sensor array.

One inventive aspect relates to a nanoantenna for use in a biosensing device, the nanoantenna being arranged to exhibit at least two SPRs and at least one of these resonances being able to excite the label by a two-photon absorption process. An advantage of an inventive aspect using a new design of nanodevice, a nanoantenna, for use in a sensor is that is allows detection at low concentration of biological components. The nanoantenna is made out of a material conductive at the relevant frequencies. Such materials are metals or semiconductors, for example.

Another inventive aspect relates to use of the nanoantenna for measuring a quantity of a biological component. Another inventive aspect relates to a nanodevice such as a nanoantenna exhibiting at least a double SPR. To achieve this, the nanoantenna can have an asymmetric structural configuration and spectrally separated resonances. Preferably there is a location in its structure providing local electromagnetic field enhancement at all of the at least two SPRs.

The nanoantenna may have a crossed dimer structure, but other structures exhibiting two or more resonances are possible. Crossed dimer structures are easy to construct and to design to provide differing resonant frequencies. Preferably the ligand or analyte to be determined is positioned at the location during detection.

Another inventive aspect relates to a substrate comprising a detection surface at the vicinity of which a quantity of biocomponents can be present, and at least one nanoantenna on top of the substrate. The substrate can also include an array of nanoantennas.

Another inventive aspect relates to a sensor having such nanoantennas exhibiting a resonance at the pumping frequency of an excitation source (e.g. laser) and at the emission frequency of a label contained in the biological component. A nanoantenna may comprise one or more antenna elements exhibiting double resonances. These resonances lead to a local electromagnetic field enhancement at one or more certain locations. The location of the field enhancement for both resonances is preferably the same. Then the label can profit from a nano-antenna pump and emission enhancement.

Another inventive aspect relates to a biosensor, comprising a nanoantenna as disclosed above with different resonances. The biosensor comprises an excitation radiation source configured to generate a signal at one frequency of the two or more SPRs of the nano-antenna, and a detector configured to detect a signal at the other frequency among the two or more SPRs of the nano-antenna.

Another inventive aspect relates to a method to determine an analyte with a label in a fluid sample using a nanoantenna having different SPRs. The method comprising generating a radiation signal at one frequency among the at least two SPRs of the nanoantenna for pumping the fluorescent label through a two photon absorption process, and detecting a luminescence radiation signal emitted by the label at a frequency which coincides with the other of the at least two surface or particle plasmon resonances (SPRs).

The label can have an absorption band in the UV or blue part of the spectrum.

The method can comprise enhancing the two-photon absorption of the label by coupling the excitation light to a SPR at one of the frequencies of the at least two SPRs of the nanoantenna.

The method can comprise enhancing the emission of the label by coupling this emission to a SPR at one of the frequencies of the at least two SPR of the nanoantenna.

When using a substrate with an array of nanoantennas, the substrate can be structured with areas in which field enhancement is different, and labels can be used with different photon absorption cross sections. This allows simultaneous analysis of multiple analytes.

Another inventive aspect relates to a method to determine an analyte with a label in a fluid sample. The method comprising generating a first radiation signal, and detecting a second radiation signal from the label. It further comprises enhancing emission of the label by exciting through a two-photon absorption process at one SPR and the coupling the label emission to a different SPR.

With embodiments of the present invention, one can excite the label at a first predetermined frequency and receive the emission of the label at a second predetermined frequency, both these frequencies being substantially different from each other. This allows efficient excitation of labels via non-linear processes like two-photon absorption and an increase of the emission efficiency of excited labels. Light sources, e.g. lasers, can be in the IR and visible part of the spectrum to excite the labels in the visible and in the UV. The use of low energy light (infrared and visible light lasers) has several advantages, e.g. reduction of photobleaching of the labels An advantage of two-photon absorption is the background free character of this technique.

Advantageously, a luminescent label having a non-linear emission process, like two-photon absorption, can be used.

In another aspect, the nanoantenna comprises a structural asymmetry, e.g. two or more different elements or different arms optionally arranged in cross configuration, each comprising two similar conductive elements. This nanoantenna is asymmetric, i.e., the arms have different lengths. In a preferred embodiment the different arms are not placed with their long axis forming a right angle, but forming the smallest angle possible. Different structural alternatives include varying the shape, dimensions, orientation of the elements, etc. The size of the nanoparticles that form the antennas may be in the range of about 10 nm to 1000 nm in a plane parallel to the plane of the carrier substrate. That is the width or length for a rectangular particle, the diameter for a particle with circular cross-section, major and minor axes for a particle with elliptic cross-section, the base of a triangle, etc. The size of the nanoparticles may in a plane perpendicular to the plane of the carrier substrate be in the range of about 10 nm to 1000 nm, for example the thickness at the thickest area of the particle.

Certain inventive aspects provide one or more advantages compared to a biosensor of the prior art, which include, for example, background free detection, improved sensitivity, low cost, ease of filtering to obtain the wanted signal, improved directionality, and low power laser source can be used.

Certain inventive aspects find application in the field of sensing, both in vitro-diagnostics (IVD) as well as air quality and food safety. The system is of value in those situations where the binding of fluorescently labelled molecules is to be detected in a large background. This is for instance the case in qPCR1 or DNA hybridization detection.

DETAILED DESCRIPTION OF CERTAIN ILLUSTRATIVE EMBODIMENTS

Although the present invention will be described in connection with certain embodiments, it is not intended to be limited to the specific form set forth herein. Rather, the scope of the present invention is limited only by the accompanying claims. In the claims, the term "comprising" does not exclude the presence of other elements or steps. Additionally, although individual features may be included in different claims, these may possibly be advantageously combined, and the inclusion in different claims does not imply that a combination of features is not feasible and/or advantageous. In addition, singular references do not exclude a plurality. Thus, references to "a", "an", "first", "second" etc. do not preclude a plurality. Furthermore, reference signs in the claims shall not be construed as limiting the scope.

Certain embodiments relate to a device, in particular a nanoantenna and a novel substrate that can be used in optical biosensing based on non-linear effects close to conductive surfaces such as nanoparticles or nanoantennas, e.g. metallic surfaces. Using this nanoantenna in a sensor it is possible to detect fluorescent labels sensitively that are bound to the surface in a fluid sample even when this contains a very large background fluorescence activity. Two-photon absorption processes is used to excite the labels. This non-linear process only takes place very close to the conductive material such as a metal, where the electromagnetic local field is enhanced and the photon density is the highest, giving rise to the suppression of the background signal. Another important advantage of two-photon absorption is that labels with absorption bands in the UV and blue part of the spectrum can be excited with visible and infrared lasers, reducing the photo-bleaching associated with high energy (high frequency) photons. The use of infrared light instead of blue light to photoexcite the labels has other very important advantages, namely the lower losses due to scattering with small inhomogeneities and specially the lower absorption of red light by blood. In this way it is also possible to obtain background-free detection in small (e.g. nanometer sized) volumes.

In certain embodiments of the present invention nanodevices such as nanoantennas are provided with resonances separated spectrally. There may be two or more resonances depending upon the shape of the nanoantenna, the length of the antenna, the width of the antenna and the number of structures that form the antenna. Local field enhancements at the same position allow enhancement of the intensity of the pump and of the emission of the labels. This can provide an enhanced sensitivity of two-photon absorption processes. The antenna is made from material conductive at the relevant frequencies, e.g. from a metal or a semiconductive material. Moreover, variation of the geometry of the nanoantenna, e.g. by structured metal shapes, gives rise to selectable different field enhancements. This can be used for simultaneous sensing of various different biocomponents or targets, for example.

Certain embodiments enable localized excitation and detection of fluorescent labels bound to a structured conductive surface such as a metal by using a specific local electromagnetic field enhancement close to the surface, e.g. metallic nanoantenna. The nanoantennas are structured in or on an insulating substrate such as a glass or plastic substrate. The substrate can be disposable. Without being limited by theory, it is believed that the enhanced local field close to the nanoantenna arises from the excitation of particle plasmon polaritons or SPRs, and can be used to excite a label through non-linear optical processes such as two-photon absorption. Since nonlinear processes require large electromagnetic field intensities, they are virtually absent at greater distances from the antenna, e.g. larger than a few tens of nanometers from the metal antenna, e.g. greater than 100 nm. This property leads to the reduction in any signal from labels not very close to the antenna, i.e. there is background free non-linear emission of the labels that are only very close to the nanoantenna. By designing nanoantennas with resonances at different frequencies and local field enhancement at the same position it is possible to enhance the pump light and increase the emission efficiency of the labels. These double resonance structures increase the sensitivity of two-photon absorption sensors.

Certain embodiments of the present invention provide local field enhancement around the nanoantennas that is tailored by modifying the dimensions and geometry of the structured metallic surface. By structuring substrates with areas in which the field enhancement is different, and by using labels with different two photon absorption cross sections, it is possible to design disposable substrates for the simultaneous analysis of multiple targets. One embodiment can provide inexpensive disposable substrates for background free, multi-analyte and/or ultra-sensitive detection that can be mass-produced, for example by nano-imprint techniques, and the implementation of these substrates into systems using cheap, low power lasers. Two-photon fluorescence for bio-analysis can be provided in disposable substrates for sensitive and reproducible detection of labels. The enhancement of both pump and emission proposed in one embodiment leads to higher sensitivity than provided by conventional systems.

Certain embodiments of the present invention provide metallic nanoantenna arrays as optionally disposable substrates for sensing. The nanoantennas increase the excitation efficiency of two-photon absorption processes of labels that can be pumped with a low power (e.g. <about 10 mwatt) continuous laser. They are designed in such a way that the pump light excites a SPR, which give rise to a local field enhancement in their proximity. This can limit the detection volume in an optical biosensor to distances of less than about 500 nm or less than about 100 nm or less than about 50 nm. In accordance with some embodiments the labels can be selected so that they cannot be excited by linear processes (one-photon absorption) at the frequency of the pump laser. This leads to the elimination the background signal.

Certain embodiments make use of nanoantennas with spectrally separated surface plasmon resonances. Asymmetric nanoantennas with spectrally separated resonances have been described in the context of optical data storage masks but only linear effects at the scattering resonances have been reported. The nanoantennas are such that these resonances are at the pumping laser frequency and at the label emission frequency. To make profit of these double resonant structures, the local field is enhanced at the same position for the pump and the emission. Hence the nanoantennas with spectrally separated resonances have spatial positions in their proximity which exhibit enhancement for both frequencies. This can be achieved, for example, in the centre of crossed nanoantennas, e.g. crossed dimers having arms of different lengths. To maximize the simultaneous absorption and emission enhancements the arms of the nanoantennas do not form a right angle but are at the smallest possible angle. In further embodiments, by designing properly the nanoantenna length, the direction of the emission of the label can be modified. This directional enhancement of the emission can be used in some embodiments to further increase the sensitivity of the biosensor. In yet further embodiments an increase can be achieved by maximizing the amount of light that is emitted within the numerical aperture of the optical system used for detection.

According to embodiments the nanoantennas can be fabricated using e-beam lithography. The antennas can include structures, e.g; nanorods with a length (L), a width (W) and a thickness (out of the plane of the substrate). The length may range between about 10 nm and 1000 nm, the width may range between about 10 nm and 1000 nm, and the thickness may range between about 10 nm and about 1000 nm. A spacing, e.g. the gap size D between arms of the antenna, may, for example be in the range between 1 nm and 100 nm.

According to embodiments the nanoantennas can be fabricated by using nano-imprint techniques. This can have the advantage of low cost. The dimensions can be the same as defined above.

In embodiments the plasmon resonance frequency can be tailored by changing the shape, dimensions and geometry of the nanoantennas, which gives all freedom on the choice of the pump laser and of the labels. Examples of lasers than can be used are inexpensive diode lasers at wavelengths commonly available in the telecommunications industry (e.g. 1300, 1500 nm). In embodiments the substrates are used with organic (dyes) and/or inorganic (quantum dots) labels. Much larger two photon absorption cross sections in quantum dots compared to those of organic molecules can provide an advantage for the use of quantum dots more for ultra-sensitive detection. Other advantages of quantum dots over organic labels are their higher photostability, larger stokes shift, absence of reabsorption in quantum dots making it possible to operate at higher concentrations, and their longer fluorescence life times.

In accordance with embodiments the excited labels emit light with a frequency $\omega_2$ very different from the pump frequency $\omega_1$. The emitted light frequency $\omega_2$ is higher than the pump frequency $\omega_1$. Therefore, a simple low-pass filter is sufficient to filter out scattered light from the pump on the surface and to detect the two-photon luminescence without requiring a spectrometer or monochromator to spectrally discern between excitation and emission frequencies. Since the two-photon luminescence will be typically in the UV and visible of the spectrum, standard photomulplier tubes can be used as very sensitive and economical detector.

Figure 1:
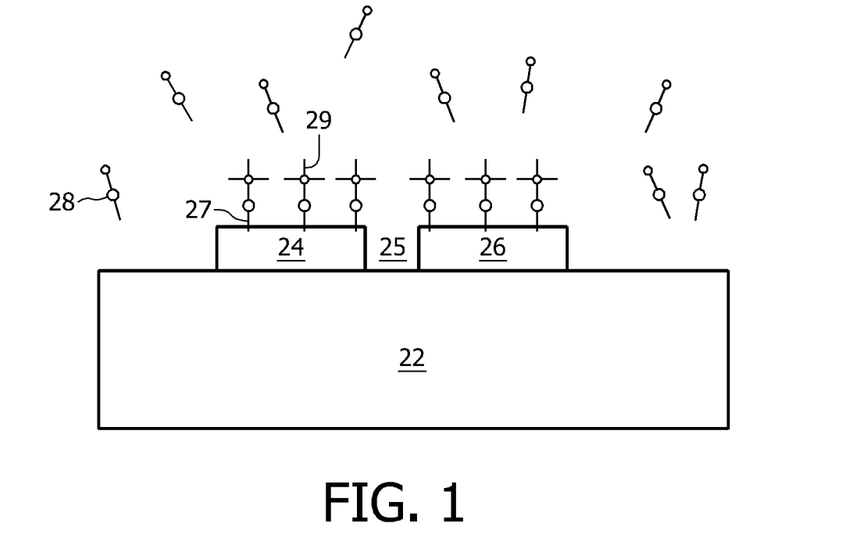
FIG. 1 shows a cross section of an antenna.

Further, the difference between $\omega_1$ and $\omega_2$ can be chosen in accordance with the desired frequency rejection and with the filter Amplitude-phase versus frequency Bode diagram that is used An embodiment of the present invention is depicted in FIG. 1. A small metal nanoantenna 20, e.g. of a noble metal such as gold or silver with a dimension in the range of about 10 to 1000 nm, or all dimensions in the range of about 10 to 1000 nm is structured on top of, or embedded in, an insulating substrate 22 such as a glass substrate. The antenna 10 has at least two arms 24, 26 (dimer antenna) separated by a gap 25 having a gap size D. The present invention is not limited to dimer antennas but includes within its scope more arms, e.g. 3 (trimer), 4 arms (e.g. crossed dimer) or more, or other structures that present two or more resonances that can be used to enhance the two-photon absorption of labels and the emission of these labels. The insulating substrate 22 may be any suitable substrate with for example, an insulating layer on its out surface. The substrate may be any substrate suitable for supporting metallic nanoparticles. The substrate may be a substrate suitable for use with a given lithographic technique. The substrate may be or may have a layer of, but is not limited to, a substrate or layer of glass, silicon, silica or a polymer.

The nature of the substrate may influence the position of the resonance peaks, and the substrate may be selected in accordance with this aspect.

The nanoparticles that form the nanoantenna may be of any type of nanoparticle exhibiting surface plasmon resonance (SPR). Examples include, but are not limited, to silicon-based substrates and metal nanoparticles, such as a nanoparticle selected from the group of Au, Ag, Pt, Pd, Al, Cr, Ti, Cu, Ru, Rh, or any combination or alloying of such or other metals. Additionally, vertical layered nanoparticles, such as multi-layer structures of the metal-insulator-metal type may be applied.

At capture sites 27, capture moieties (for instance antibodies or DNA probes with or without linkers) are placed on the metal surface, e.g. non-covalently or covalently bound to or retained on the metal surface by a binding means. Noble metals, and especially gold bind many bio-molecules. The capture moieties bind to ligands such as macro-molecules, biomolecules, DNA, RNA, antigens, nucleic acids, amino acids, proteins, cells, bacteria, virus, fungus, micro tubili, various drug molecules, etc. The capture moieties may be functionalized by chemical receptors, or receptor molecules. Receptor molecules, as known in the art, are capable of selectively binding specific molecules or ligands, such as macro-molecules, biomolecules, DNA, RNA, antigens, nucleic acids, amino acids, proteins, cells, bacteria, virus, fungus, micro tubili, various drug molecules, etc. The receptor molecules may be exposed to a molecular species which they bind, resulting in modified molecular binding complexes which bind to the nanoparticles.

A fluid is then added that contains biocomponents or target molecules 28. The target molecules will selectively bind at the capture sites 27 to the capture moieties. The target molecules 28 can be labeled directly (e.g. in case of DNA) or one or more second labeled moieties 29 can be used to form a complex. Labels in the proximity of the metal are excited by two-photon absorption processes, producing an optical signal. Labels far from the metal surface of the antenna (e.g. at a distance larger than 50 nm) are not excited (or only to a limited extent) and they do not contribute to the emitted signal. The fluorescent labels are excited by a two-photon absorption process when the nanoantenna 20 is illuminated with light of frequency equal to the plasmon resonance frequency. Since the two-photon fluorescence intensity depends quadratically on the pump intensity, a signal is only generated where this intensity is large. The near field of the total electric field is different for nanoantennas with different geometries (e.g. larger or smaller gap distance between the arms). The near field intensity of the total electric field at the longitudinal resonance for an antenna is much higher with strongly coupled arms of the antenna (e.g. FIG. 1: gap size D=20 nm, arm length L=110 nm) compared to an uncoupled antenna (e.g. gap size D=100 nm, L=110 nm). The near field intensity is locally increased by orders of magnitude, e.g. two orders of magnitude for the coupled nanoantenna in comparison to the uncoupled antenna. For a larger gap D between the arms of the antenna, the field enhancement is lower than when the distance of between arms is small, i.e. more strongly coupled antenna arms. This difference can be used to perform simultaneous analysis with different labels with the same substrate.

The SPR of a nanoantenna depends on the length of the arms 24, 26 of the nanoantenna and on the size of the gap 25 between the antenna arms. For example, the SPR wavelength of dimer nanoantennas as a function of the antenna arm length and of the antenna gap width can be calculated or measured. The surface plasmon resonance wavelength is a function of the antenna arm length and of the antenna gap width. For example for Au an arm length of 85 nm and a gap of 20 nm, or an arm length of 100 nm and a gap length of 40 nm or an arm length of 110 nm and a gap length of 70 nm all lead to a plasmon resonance frequency of about 700 to 750 nm, e.g. 730 nm. An arm length of 80 nm and a gap of 70 nm leads to a plasmon resonance frequency of about 650 to 670 nm, e.g. 660 nm.

In embodiments of the present invention the sensitivity of the biosensor based on two-photon absorption is increased further by enhancing also the emission of the labels by coupling this emission to a SPR. In accordance with one embodiment to achieve enhancement of both the pump and the emission, nanoantennas are provided which have resonances at very different frequencies. Hence, embodiments makes use of asymmetric nanoantennas with spectrally separated resonances. Preferably, local field enhancements are provided at the same location (25) for these frequencies. The last requirement has the advantage that both the pump and the emission will be enhanced in each label. To achieve the same location for the two local field enhancements, the nanoantenna has a structure having at least one location that is bordered by antenna elements that, in combination, exhibit resonances at both frequencies.

Figure 2:
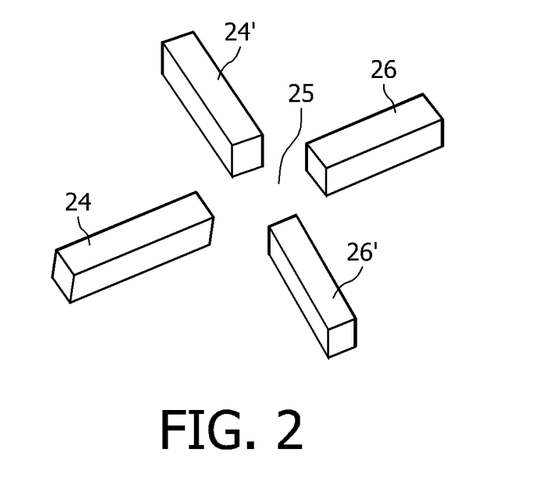
FIG. 2 shows an artistic representation of an antenna in accordance with an embodiment of the present invention.

For example, in accordance with an embodiment of the present invention, a cross shaped nanoantenna (crossed dimer), as the one depicted in FIG. 2, formed by two orthogonal and distinct dimers has the advantage of a large field enhancement in its centre. The crossed dimer antenna is an asymmetric nanoantenna with spectrally separated resonances. The two dimers forming the crossed antenna structure have arms 24, 26 and 24' and 26' respectively and a central gap 25. The two dimers have a different arm length and/or gap, and are therefore resonant at different frequencies. By careful selection of the dimensions, one of the dimers will resonate at the pump frequency and the other at the emission frequency. Only labels placed in the centre of the cross will feel both an enhanced pump intensity and an enhanced emission efficiency. Note that labels with a dipole moment oriented parallel to one of the arms will only couple this arm. Therefore, to maximize the pump and emission enhancements the arms of different length should be placed as parallel as possible and the labels aligned with dipole moment in this direction.

Figure 3:
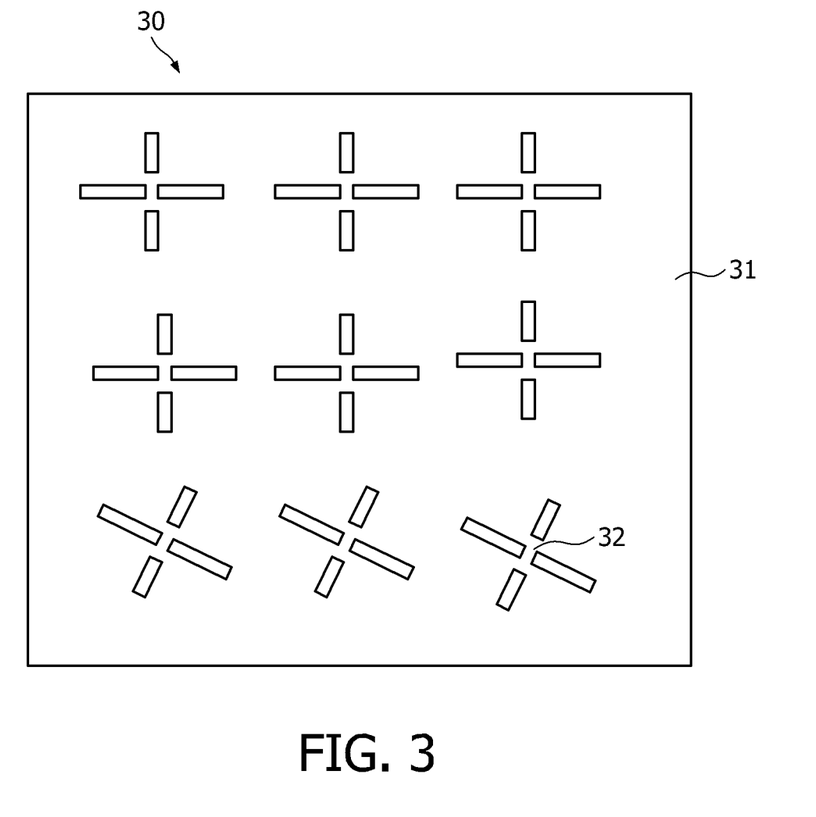
FIG. 3 shows an array of antennas in accordance with an embodiment of the present invention.

In a further embodiment the nanoantennas can be formed into arrays, e.g. arrays of dimers, trimers, crossed dimers, etc., i.e. having asymmetric nanoantennas with spectrally separated resonances. Arrays of nanoantennas can be used to increase the number of labels coupled to them. FIG. 3 schematically illustrates a sensor array 30. The sensor array comprising a substrate 31, and a plurality of nanoantennas or nanoparticles (nano-sized particles) 32 according to certain embodiments of the present invention (e.g dimers, trimers, crossed dimers, etc, the nanoantennas exhibiting a multi frequency response, e.g. resonances at two or more frequencies) disposed on the substrate. A sensor array may comprise a plurality of areas. All areas can be identical in that these areas comprise the same number of nanoantennas and have the same design. However, a sensor array may comprise a number of different areas may be provided. A sensor array comprising a plurality of areas may e.g. be used as a bio-array or micro-array. For example, different area may be functionalized with different chemical receptors, alternatively the entire sensor array may be functionalized with the same chemical receptors, and different areas may be exposed to different target molecules. The different array on the sensor array may e.g. be functionalized, or exposed to a target solution, by application of drop deposition from pulsejets, or by other suitable means. A sensor array comprising a plurality of areas may be applied in connection with a bioassay.

In accordance with one embodiment of the present invention, for each of the nanoparticles a structural parameter of the nanoparticles, or a group of nanoparticles, is correlated to an associated SPR. Moreover, for the plurality of nanoparticles, the structural parameter and thereby the SPR can be varied in a pre-defined way in at least a first area of the substrate. The variation of the structural parameter can be a variation in the length of a nanoparticles arm of a nanoantenna and/or a gap size between arms of the antennas along a direction in the array. The variation of the structural parameter in a pre-defined way, include, but are not limited to, a structural variation along a predefined direction, for example, along the vertical direction or any other direction in the surface plane of the carrier substrate. Also the orientation of the nanoantennas 32 may be vary in the array 30.

The sensor array may be fabricated by using a lithographic technique, including but not limited to e-beam lithography, optical lithography, focused ion-beam lithography and nano-imprinting lithography. Moreover, it is envisioned by the inventors that improved techniques including techniques based on self-assembly or other bottom-up techniques as well as next-generation lithography, for example high-index immersion lithography, extreme ultraviolet lithography (EUV-lithography), X-ray lithography can be applied as they become available. A serial lithography technique, such as e-beam lithography, may advantageously be applied for small-scale production since specific nanoparticle shapes can be produced. A parallel lithography technique, such as nano-imprint lithography, may advantageously be applied for large-scale production, since it requires the production of a stamp.

Figure 4:
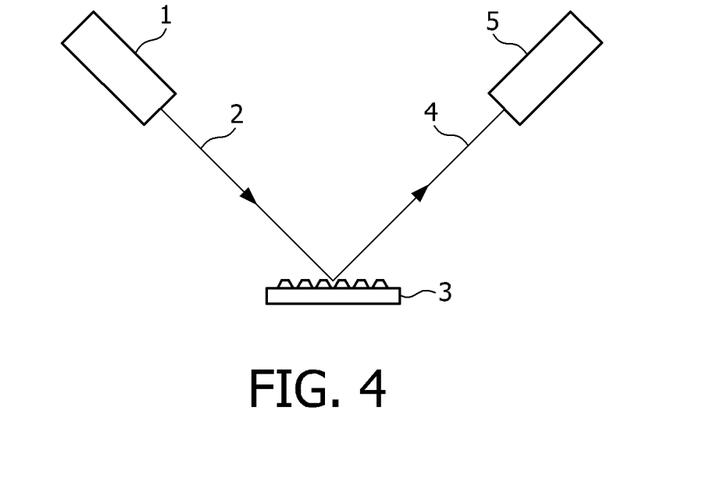
FIG. 4 shows a schematic arrangement of a detection system for use with one embodiment.

FIG. 4 schematically illustrates a general overview of an optical detection system in accordance with certain embodiments of the present invention using an array. A radiation source 1 emits excitation radiation 2 onto a sensor surface 3. The excitation radiation excites a SPR on the sensor, and the emitted radiation 4 is detected by a radiation detector 5 in order to analyse the interaction between the excitation radiation and the sensor. At some or each location on the array a nanoantenna according to certain embodiments of the present invention is located, e.g. asymmetric nanoantennas with spectrally separated resonances. At least some of the nanoantennas exhibit a multi frequency response, e.g. resonances at two or more frequencies.

The number of spots on a bio-array may vary from around 1 to 1000 pr. mm2, and even higher, e.g. up to 106 spots pr. mm2.

In further embodiments antennas with other particle shapes different from beam or rod-shaped particles can be used, e.g. antennas with polygonal antenna elements such as triangle dimers or other shapes such as bowties, can be used in order to tune the SPR by antenna shape and structure. These alternative designs are also structured as asymmetric nanoantennas with spectrally separated resonances. Preferably there is one location in the antennas and/or their surroundings where enhancement at both frequencies occurs. For example, dimers having antenna elements can be formed in a crossed structure to provide two different plasmon resonance frequencies, e.g. at the pump and emission frequencies. A bowtie gold nanoantenna can be formed, for example by two triangular particles close to each other. Crossed shaped bowtie nanoantennas can be used to enhance both the pump and emission of the label. Included within the scope of this invention is any antenna structure that shows a clear spectral resonance and a large electromagnetic enhancement and exhibits spectrally separated resonances.

In a further embodiment multianalyte sensing is provided using tunable lasers, (e.g. with nanoantennas that are all the same) and/or nanoantennas with different shapes and dimensions having different near field enhancement and different SPRs. Both of these techniques can be used to provide substrates for simultaneous analysis of different biomolecules with different labels. An example of such a substrate is formed from clusters of nanoantennas, each cluster having antennas with the same dimensions. Adjacent clusters have nanoantennas with different dimensions, thus different field enhancement at the pump and/or emission frequency. If an assay contains biomolecules with labels having different two-photon absorption cross-sections, more or less two-photon fluorescence will be detected depending of the field enhancement. This will depend on the cluster and hence a distinction can be made depending on which cluster emits a signal. The field enhancement can be tuned by changing the shape and dimensions of the nanoantennas, or by tuning the wavelength of the pump laser. Tunable lasers allow thus multianalyte sensing on substrates with just one type of nanoantennas when labels with different absorption cross sections are used.

In further embodiments readout methods are provided either by parallel imaging of the intensities using a camera such as a CCD or CMOS camera, or by subsequent scanning of the particles. The direct imaging method is commonly used in commercial DNA microarray analysis equipment, while the scanning method may be compatible with other sensing devices.

Figure 5:
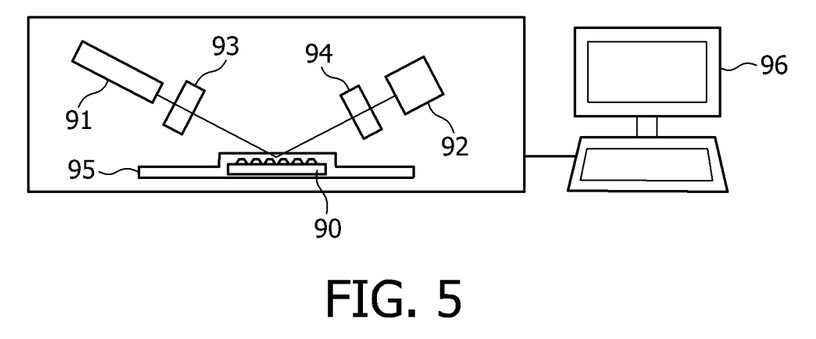
FIG. 5 shows a further schematic arrangement of a detection system for use with one embodiment.

FIG. 5 illustrates an embodiment of an optical detection system for detecting a target. The optical system comprises a sensor array 90 in accordance with certain embodiments of the present invention i.e. having an array of nanoantennas exhibiting at least two different plasmon resonance frequencies. Moreover a radiation source 91 is present, typically in the form of a monochromatic laser source, and a detector 92 for detecting the photoluminescence light after interaction with the sensor array. In addition to these elements, the optical system may comprise optical elements 93, 94, such as filters, polarizers, beam splitters, etc., placed in the beam path before (93) the sensor array and/or after (94) the sensor array. In accordance with an embodiment of the present invention a simple filter is used as the optical element 94. Also a sample handling system 95, such as a liquid flow cell or other means for exposing a gaseous or liquid solution to the sensor surface, may be present. Moreover, the detection system may comprise or be connected to a computer system 96, for control of the detection system and for processing and possible displaying the obtained detection results. The radiation source 91 may be a tuneable laser source for emitting monochromatic radiation at a number of selectable wavelengths or an LED or a set of LEDs. The light may illuminate the whole array or may be focussed onto a spot that can be scanned through the sensor array. The detector may be a photodetector, such as a spatially resolved detector e.g. a CDD-based detector or a CMOS camera. A non-spatially resolved detector, such as a photodiode or a PMT, may also be applied. The optical detection system, may also comprise or be connected to additional sample handling units, such as a unit for contacting the substrate with a target. The optical detection system may be automated or semi-automated.

In FIG. 5 a specific optical setup is illustrated. It is however to be understood that the invention is not limited to this setup. The angle of incidence may in general range from perpendicularly incident from the top to perpendicularly incident from the bottom, as long as it is possible to excite SPRs of the supported nanoparticles. Moreover, the radiation may be polarized, and especially may be a variation between an angle of polarization and an orientation or arrangement of the nanoparticles be applied in order to detect intensity variations.

Figure 6:
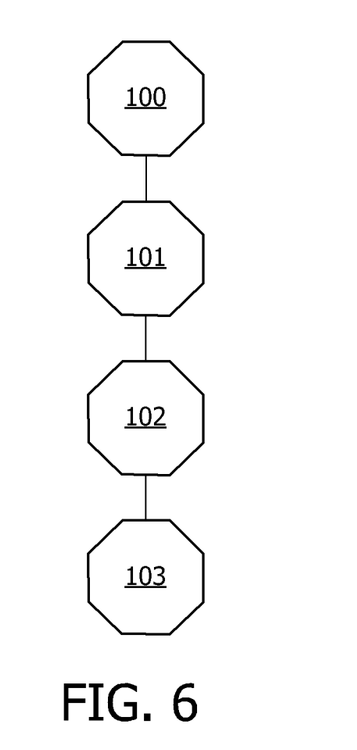
FIG. 6 shows flow diagram of a method according to one embodiment.

A large number of different types of measurements may be made by a sensor array in accordance with certain embodiments of the present invention. A measurement may comprise, but are not limited to steps as illustrated in FIG. 6. In steps prior to the steps of FIG. 6, a sensor array has been prepared. Followed by the blocks:

100: the sensor array is exposed to the target;

101: the sensor array is exposed to excitation radiation capable of exciting as SPR a surface plasmon resonance (SPR) on the sensor array; and

102: the resulting radiation is detected with a radiation detector after interaction with the sensor array.

Optionally, if the array contains nanoantennas with different structural parameters and hence different plasmon resonance frequencies, a step 103 may be added: detecting intensity variations in the resulting radiation, and correlating the intensity variation to the pre-defined variation in the structural parameter in order to detect the presence of the target.

In one embodiment, such parameters as particle size, pre-defined structural parameter, excitation wavelength, etc. are disclosed in connection with description of different embodiments. It is to be understood a large number of variations within the scope of the invention is possible for the skilled person. Moreover, in a measurement, a number of parameters may need to be correlated. For example, a sensor array with a specific type of structural variation may be selected in accordance with a desired target to be detected. The excitation wavelength may be correlated with nanoparticles, or vice versa. Also a specific carrier substrate may be selected, etc.

The foregoing description details certain embodiments of the invention. It will be appreciated, however, that no matter how detailed the foregoing appears in text, the invention may be practiced in many ways. It should be noted that the use of particular terminology when describing certain features or aspects of the invention should not be taken to imply that the terminology is being re-defined herein to be restricted to including any specific characteristics of the features or aspects of the invention with which that terminology is associated.

While the above detailed description has shown, described, and pointed out novel features of the invention as applied to various embodiments, it will be understood that various omissions, substitutions, and changes in the form and details of the device or process illustrated may be made by those skilled in the technology without departing from the spirit of the invention. The scope of the invention is indicated by the appended claims rather than by the foregoing description. All changes which come within the meaning and range of equivalency of the claims are to be embraced within their scope.

What is claimed is:

1. A luminescent biosensor comprising:
   a nanoantenna adapted to measure a quantity of a biological component comprising a label, the nanoantenna being arranged to exhibit at least two particle plasmon resonances or surface plasmon resonances (SPRs), at least one of the resonances being able to excite the label by a two-photon absorption process;
   an excitation radiation source configured to generate a signal at one frequency of the at least two surface or particle plasmon resonances (SPRs) of the nano-antenna; and a detector configured to detect a signal at the other frequency among the two surface or particle plasmon resonances (SPRs) of the nano-antenna.

2. The biosensor according to claim 1, further comprising a crossed dimer structure.

3. The biosensor according to claim 2, wherein the dimer structure comprises two arms having respective long axis forming an angle smaller than 90° with respect to each other.

4. The biosensor according to claim 2, wherein the dimer structure comprises two arms having respective long axis of different length.

5. The biosensor according to claim 1, further comprising at least one ligand for binding to a part of the antenna.

6. The biosensor according to claim 1, wherein the nanoantenna is made of metal, and the label is photoluminescent.

7. The biosensor according to claim 1, wherein the label has a predetermined emission frequency, and at least one of the resonances is able to couple to this emission frequency.

8. The biosensor according to claim 1, further comprising a substrate comprising a detection surface at the vicinity of which the biological component is present, wherein the nanoantenna is formed on the substrate.

9. The biosensor according to claim 1, wherein the biosensor comprising an array of the nanoantennas.

10. An apparatus for determining an analyte with a label in a fluid sample using a nanoantenna, the nanoantenna being configured to exhibit at least two particle plasmon resonances or surface plasmon resonances (SPRs), the apparatus comprising:

means for generating a radiation signal at one frequency among the two surface or particle plasmon resonances (SPRs) of the nanoantenna for pumping the label through a two-photon absorption process; and means for detecting a luminescence radiation signal emitted by the label at a frequency which coincides with the other of the at least two surface or particle plasmon resonances (SPRs).

11. The apparatus according to claim 10, wherein the nanoantenna is made of metal, and the label is photoluminescent.

12. The apparatus according to claim 10, wherein the label has a predetermined emission frequency, and at least one of the resonances is able to couple to this emission frequency.

* * * * *